United States Patent
Pazienza et al.

(10) Patent No.: US 6,821,292 B2
(45) Date of Patent: Nov. 23, 2004

(54) CRIMPABLE INTRALUMINAL ENDOPROSTHESIS HAVING HELICAL ELEMENTS

(75) Inventors: John D. Pazienza, Pompano Beach, FL (US); Peter G. Piferi, Plantation, FL (US); Gary J. Becker, Miami, FL (US)

(73) Assignee: Orbus Medical Technologies Inc., Fort Lauderdale, FL (US)

( * ) Notice: Subject to any disclaimer, the term of this patent is extended or adjusted under 35 U.S.C. 154(b) by 149 days.

(21) Appl. No.: 10/071,071

(22) Filed: Feb. 8, 2002

(65) Prior Publication Data

US 2002/0111669 A1 Aug. 15, 2002

Related U.S. Application Data

(63) Continuation-in-part of application No. 09/511,481, filed on Feb. 23, 2000, which is a continuation of application No. 09/094,402, filed on Jun. 10, 1998, now Pat. No. 6,117,165.
(60) Provisional application No. 60/267,778, filed on Feb. 9, 2001.

(30) Foreign Application Priority Data

Jun. 13, 1997  (EP) ............................................ 97201799
May 6, 1998  (EP) ............................................ 98201446

(51) Int. Cl.$^7$ ................................................ A61F 2/06
(52) U.S. Cl. ..................... 623/1.15; 623/1.17; 623/1.22; 623/1.16
(58) Field of Search ........................... 623/1, 12, 11.11, 623/66.1; 606/191–198

(56) References Cited

U.S. PATENT DOCUMENTS

| | | | |
|---|---|---|---|
| 5,741,327 A | 4/1998 | Frantzen | 623/1 |
| 6,136,023 A | 10/2000 | Boyle | 623/11 |
| 6,171,334 B1 | 1/2001 | Cox | 623/1.15 |
| 6,190,403 B1 | 2/2001 | Fischell et al. | 623/1 |
| 6,264,689 B1 * | 7/2001 | Colgan et al. | 623/1.22 |
| 6,331,189 B1 | 12/2001 | Wolinsky et al. | 623/1.16 |
| 6,340,366 B2 | 1/2002 | Wijay | 623/1.13 |
| 2002/0116644 A1 * | 8/2002 | Cottone et al. | 623/1.2 |

FOREIGN PATENT DOCUMENTS

WO        WO 9939660 A1 *  8/1999 ............. A61F/2/06

* cited by examiner

Primary Examiner—David J. Isabella
Assistant Examiner—Urmi Chattopadhyay
(74) Attorney, Agent, or Firm—White & Case LLP (57) ABSTRACT

A stent having helical elements, a geometry for improved crimping, and a good stent-to-vessel ratio is disclosed. In one embodiment, the stent has a plurality of first helical segments and a plurality of second opposing helical segments. The first helical segments are comprised of a plurality of first expandable elements and the second helical segments are comprised of a plurality of second helical elements. The expandable elements are joined to each other by a plurality of struts. When the stent is crimped a portion of one of the first expandable elements nest within another portion of the same expandable element and a portion of two first expandable elements nestle between the same two portions of second expandable elements.

33 Claims, 7 Drawing Sheets

& # x 20; # CRIMPABLE INTRALUMINAL ENDOPROSTHESIS HAVING HELICAL ELEMENTS

This application claims the benefit of U.S. Provisional Application No. 60/267,778, filed on Feb. 9, 2001, which is hereby incorporated in its entirety by reference, and it is a continuation-in-part of U.S. patent application Ser. No. 09/511,481, filed on Feb. 23, 2000, which is also hereby incorporated in its entirety by reference and which is a continuation of U.S. patent application Ser. No. 09/094,402, filed Jun. 10, 1998 (now U.S. Pat. No. 6,117,165).

BACKGROUND OF THE INVENTION

1. Field of the Invention

The present invention relates to intraluminal endoprosthetic devices known as stents. In particular, the present invention relates to stents having helical elements with a geometry that allows the stent to be readily crimped onto a delivery device.

2. Description of Related Art

Stents are prosthetic devices that are implanted in the lumen of a vessel inside the body to provide support for the vessel's wall. Structural support from stents is particularly important in angioplasty procedures. Typically, stents are implanted within a vessel system to reinforce vessels that are partially occluded, collapsing, weakened, or abnormally dilated. More generally, stents can be used inside any physiological conduit or duct, including—for example— arteries, veins, bile ducts, the urinary tract, alimentary tracts, the tracheobronchial tree, a cerebral aqueduct or the genitourinary system. Stents may be used in both humans and animals.

There are typically two types of stents: self expanding stents and balloon expandable stents. Self expanding stents automatically expand once they are released and assume a deployed, expanded state. A balloon expandable stent is expanded using an inflatable balloon catheter. The balloon is inflated to plastically deform the stent. Balloon expandable stents may be implanted by mounting the stent in an unexpanded or crimped state on a balloon segment of a catheter. The catheter, after having the crimped stent placed thereon, is inserted through a puncture in a vessel wall and moved through the vessel until it is positioned in the portion of the vessel that is in need of repair. The stent is then expanded by inflating the balloon catheter against the inside wall of the vessel. Specifically, the stent is plastically deformed by inflating the balloon so that the diameter of the stent is increased and remains at an increased state. In some situations, the vessel in which the stent is implanted may be dilated by the stent itself when the stent is expanded.

The Palmaz-Schatz™ stent, which is disclosed in the *Handbook of Coronary Stents* by Patrick W. Serruys et al. (Martin Dunitz, LTD 1998), is an example of a balloon expandable stent that had been implanted in hundreds of thousands of patients. The Palmaz-Schatz™ stent, like other known stents, has certain limitations. These include, but are not limited to: (i) low stent-to-vessel ratio uniformity, (ii) comparative rigidity of the stent in a crimped as well as deployed state, and (iii) limited flexibility making delivery and placement in narrow vessels difficult. Stent-to-vessel ratio generally refers to the degree that the vessel wall is supported by the stent in its expanded state and preferably should be uniform throughout the length of the stent. Furthermore because the Palmaz-Schatz™ stent consists of one or more bridges that connect a number of consecutively slotted tubes, there are a number of bare areas in the vessel after the expansion of the stent. These shortfalls are common to many stents. Id. at 36.

SUMMARY OF THE INVENTION

The present invention is directed to expandable stents that have geometries that allow them to be readily crimped onto a balloon delivery device. In one embodiment, the stent may be comprised of a plurality of first helical segments having a first helical angle with respect to the longitudinal axis of the stent and a plurality of second helical segments that have a second helical angle. The helical segments are capable of expanding and contracting circumferentially, i.e., they expand or contract along the circumference of the stent. In this embodiment, when the stent is crimped, at least one portion of one first helical segment, along with at least one portion of a second first helical element, nestle between the same two portions of two separate second helical segments.

In one embodiment of the present invention, the stent is comprised of a plurality of first expandable elements and a plurality of second expandable elements. The first expandable element may have a segment that nests within another segment of the same first expandable element. In some embodiments, the first expandable elements are joined together by struts to form first helical segments and the second expandable elements are joined together by struts to form second helical segments. The first and second helical segments may have different helical angles or different pitches. In some embodiments, the first and second helical segments share common struts.

In some embodiments of the present invention, the stent may be comprised of a plurality of cells. Each cell may be comprised of first and second elements that are alternatively joined together (i.e., each first element is joined to two second elements and each second element is joined to two first elements to form a polygon). The polygon may be amorphous or may have a definite shape. When the stent is crimped a portion of each first of the elements that make up the cell nestles between portions of the second elements of the cell. In some embodiments, the first and second elements may touch each other when the stent is crimped. A plurality of struts joins the cells to form a stent body. In addition portions of a first element may nest within other portions of the same first element and a portion of a second element may also nest within a portion of the same first element.

BRIEF DESCRIPTION OF THE DRAWINGS

FIG. 8b is an enlarged portion of one of the cells shown in FIG. 8a.

DETAILED DESCRIPTION OF THE INVENTION

The present invention is directed to an expandable stent having a geometry that is well-suited for crimping the stent onto a delivery device. In some, but not necessarily all embodiments of the present invention, the stents may have an expanded diameter that as 3 to 6 times that of its crimped diameter. In addition, in some—but not necessarily all—embodiments the stent-to-vessel ratios may be better than approximately 15%.

Figure 1:
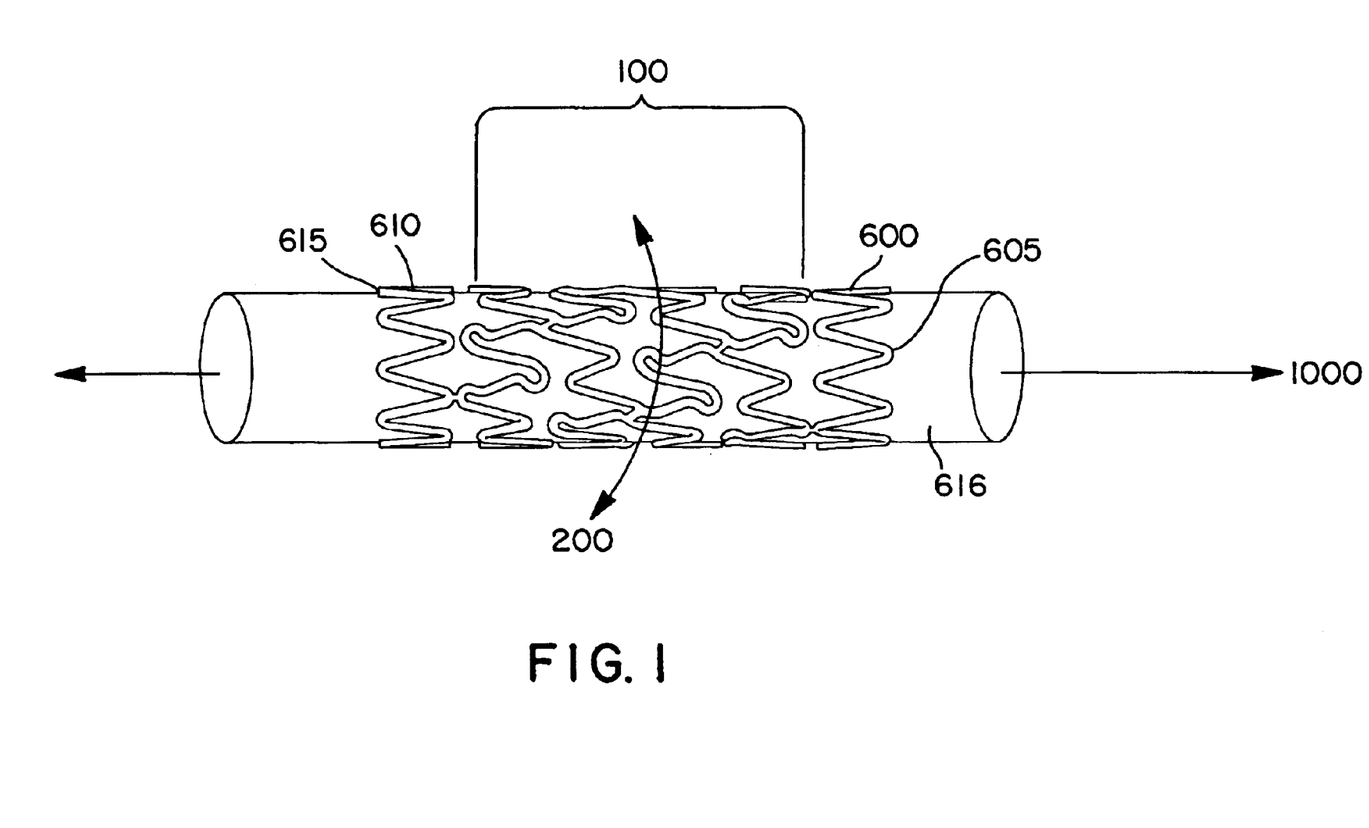
FIG. 1 is a three dimensional view of one embodiment of a stent according to the present invention.
Figure 2:
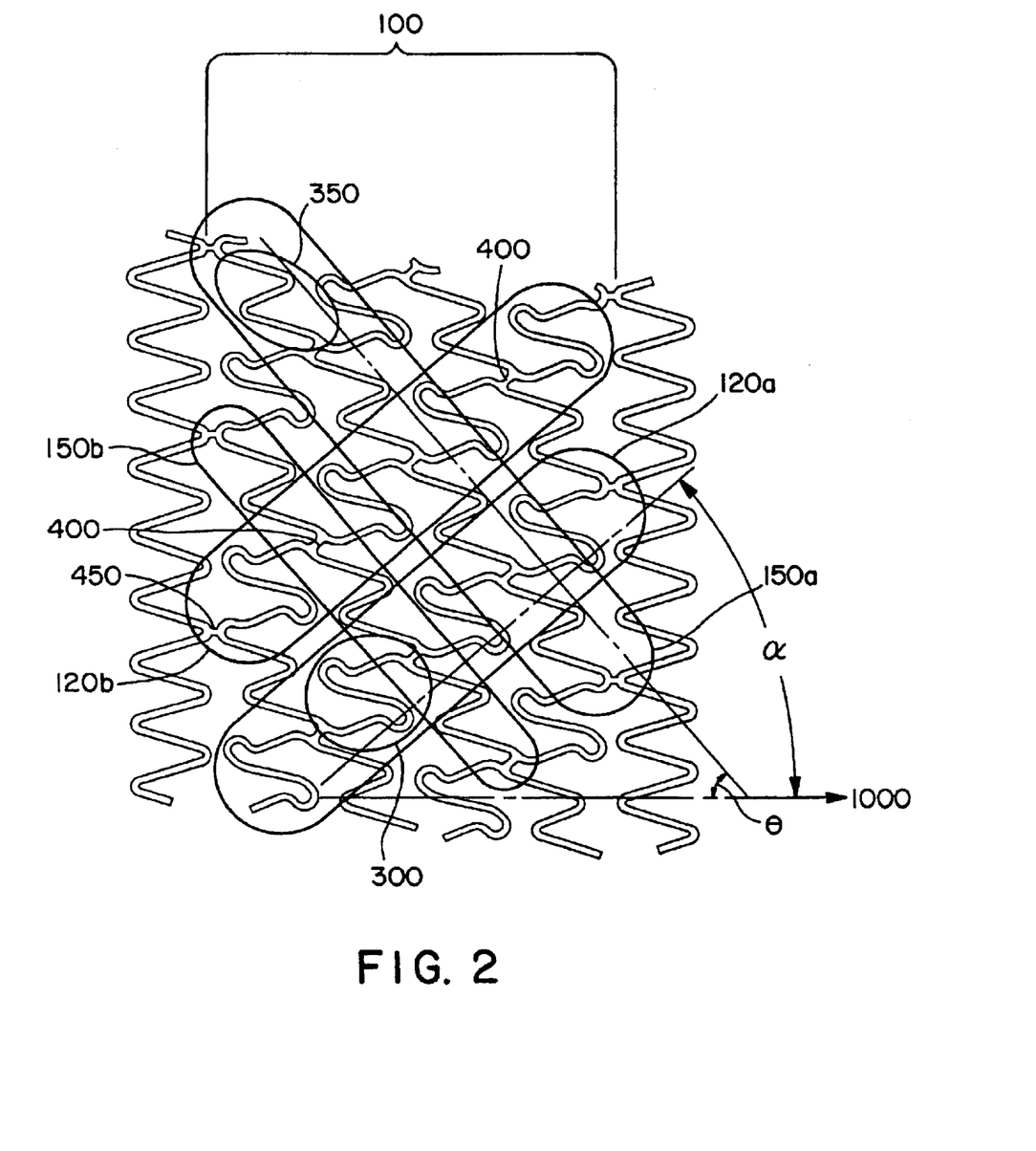
FIG. 2 is planar view of a flattened portion of the circumference of the stent in FIG. 1.

In one embodiment of the present invention, as is shown in FIGS. 1 & 2, a stent is comprised of a main body section 100 having a longitudinal axis 1000. The stent shown in FIG. 1 is mounted on a carrier 616. The main body is comprised of a plurality of first helical segments 120a and 120b and a plurality of second helical segments 150a and 150b. The first helical segments form a helical angle α with respect to the longitudinal axis 1000 of the stent, resulting in the first helical segments having a first pitch. The second helical segments 150a and 150b form a helical angle θ with respect to the longitudinal axis 1000, resulting in the second helical segments having a second pitch. In some embodiments α varies between 20° and 50°, and θ varies between 20° and 90°. The first helical segments 120a and 120b and second helical segments 150a and 150b are circumferentially expandable, i.e., they are capable of expanding in a direction parallel to the direction of the circumference 200 of the stent. The helical segments 120a, 120b, 150a, and 150b also circumferentially contract when the stent is crimped.

As is discussed further below, in some embodiments, the first helical segments 120a and 120b may be comprised of a plurality of filament segments and likewise the second helical segments 150a and 150b may be comprised of a plurality of filament segments. In some embodiments the total length of the sum of all the filament segments comprising the first helical segment may be longer than the total length of the filament segments comprising the second helical segment. In some cases, the first and second helical segments may share common filament segments.

As is shown in FIG. 2, the first helical segments 120a and 120b are comprised of a plurality of first expandable elements 300, and the second helical segments are comprised of a plurality of second expandable elements 350. Two or more first expandable segments 300 are joined together by a plurality of struts 400 to form each of the first helical segments 120a and 120b. The same struts 400 also join two second expandable segments 350 to form the second helical segments 150a and 150b. The struts 400 may be an integral part of the first or second expandable element, or both.

Figure 3:
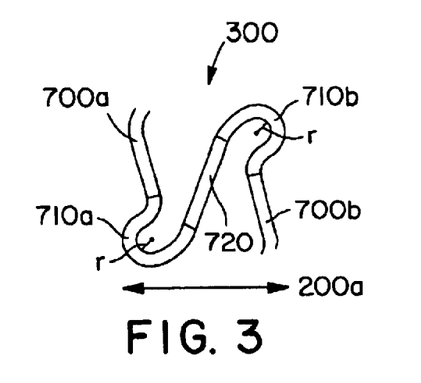
FIG. 3 is a planar view of one element that makes up the stent body as shown in the planar view of FIG. 2.
Figure 4A:
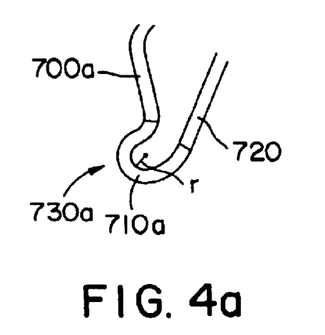
FIGS. 4a and 4b are views of filament segments that comprise the element shown in FIG. 3
Figure 4B:
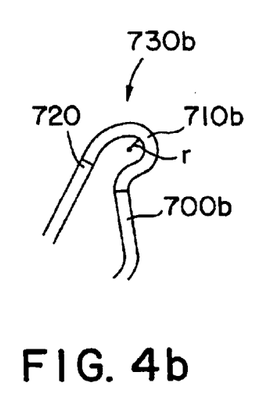

As is shown in FIG. 3, in some embodiments, the first expandable elements 300 are comprised of a plurality of contiguous filament segments 700a, 700b, 710a, 710b and 720. In one embodiment, the filament segments 700a, 710a and 720 are joined together to form a generally R-shaped structure 730. (See FIG. 4). The filament that forms the head of the R, i.e. filament 710a or 710b, may be curved and have a radius r. The radius r may take many values, including but not limited to approximately 0.015 inches. As is shown in FIGS. 3, 4a, and 4b, the first expandable elements 300 may be comprised of a plurality of R-shaped structures 730a and 730b oriented inversely to one another and sharing a common filament segment 720.

Figure 5:
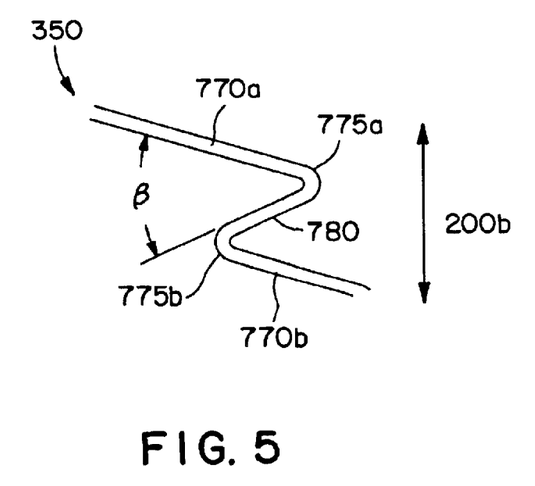
FIG. 5 is a planar view of a second element that makes up the stent body shown in FIG. 2.

In some embodiments, as is shown in FIG. 5, the second expandable elements 350 may be comprised of a plurality of contiguous filament segments 770a, 770b, 775a, 780, and 775b and may, for example, in some embodiments form a Z-shaped structure. For example, as is shown, filament 770a may lie at an angle β with respect to filament 780 and segments 770a and 770b may be joined to the single segment 780 by curved segments 775a and 775b. In some, but not necessarily all, embodiments, 770a and 770b have the same dimensions, and 780 may be shorter. The angle β may also vary greatly, and in one embodiment ranges between 30° and 40°, for example.

As is shown in FIG. 1, some embodiments of the present invention may have endzones 600 & 610 that straddle the main body 100. The endzones may have square outer edges 605 & 615. The endzones may be attached to the main body 100 with a plurality of second struts 450. (See FIG. 2). The second struts may have an orientation that differs from that of the other struts 400. For example, the second struts 450 may be parallel to the cylindrical axis 1000 of the stent, while the struts 400 may be oriented at an angle to the cylindrical axis of the stent.

The stents of the present invention provide a geometry that improves their crimpability. For example, one embodiment of the present invention may have a crimped diameter of less than 2.0 mm and an expanded diameter of 6.0–12.0 mm, or greater. The stent may be crimped onto a PTA Balloon at a diameter of 1.50 mm and it may be manufactured from a tube having a diameter of approximately between 0.03 to 0.500 inches. Of course, other sized tubes may be used. And stents may be manufactured in a wide variety of sizes for a wide variety of applications.

Figure 6:
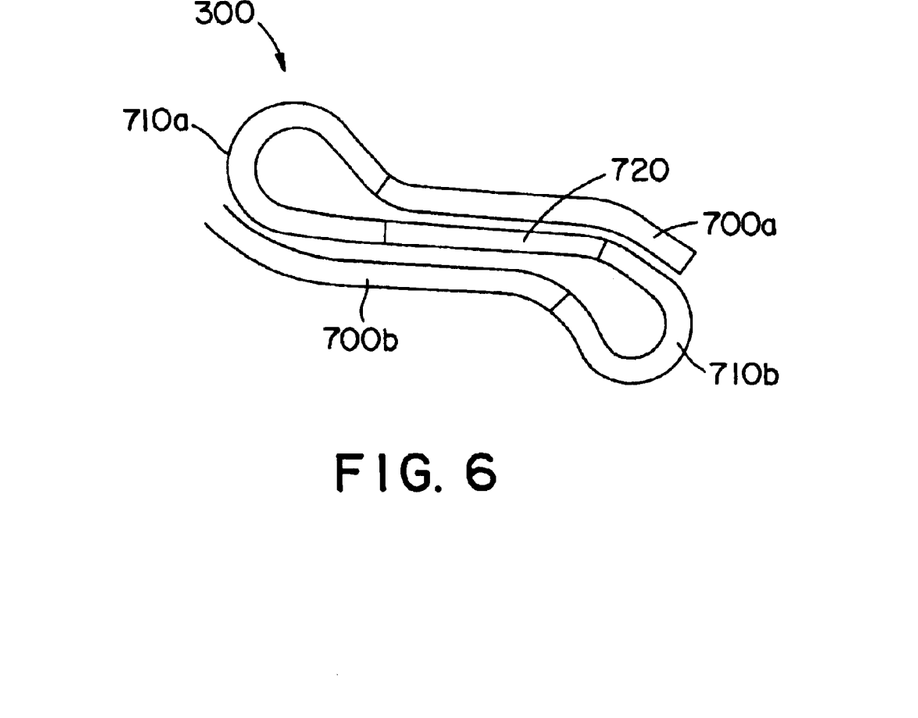
FIG. 6 is a planar view of the element of FIG. 3, when the stent is crimped.

In one embodiment of the present invention, when the stent is crimped, a first portion of the first expandable element 300 nests within another portion of the same first expandable element 300. For example, as is shown in FIG. 6, portions of filament 710a and 720 nest within a concave portion of filament 700b. Likewise portions of filaments 710b and 720 nest within a concave portion of filament 700a.

Figure 7:
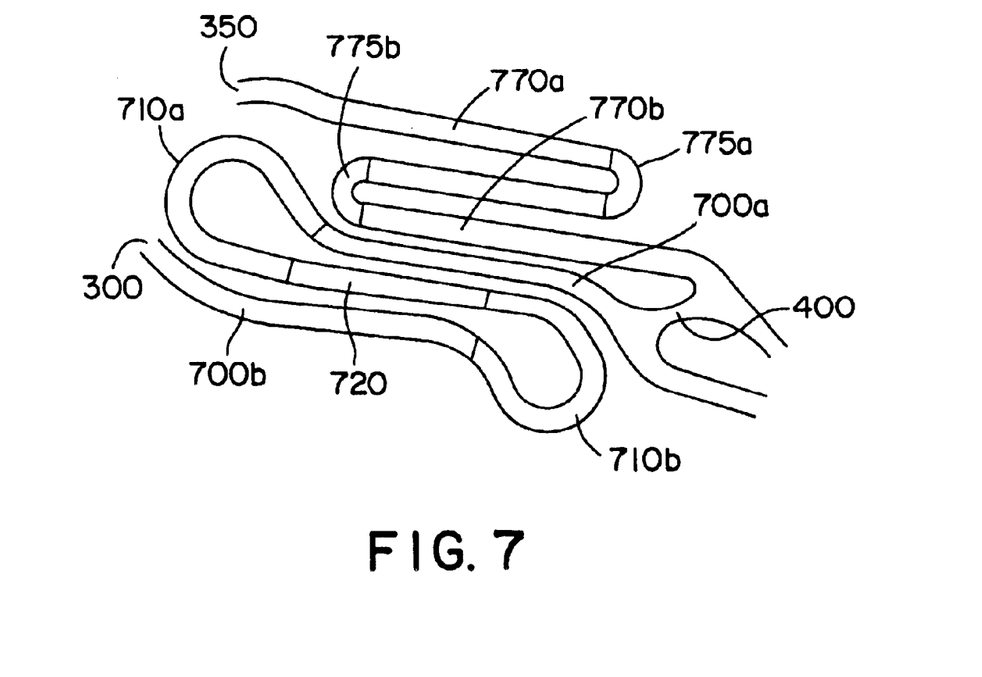
FIG. 7 is a planar view of the elements of FIGS. 3 and 5, when the stent is crimped.
Figure 10:
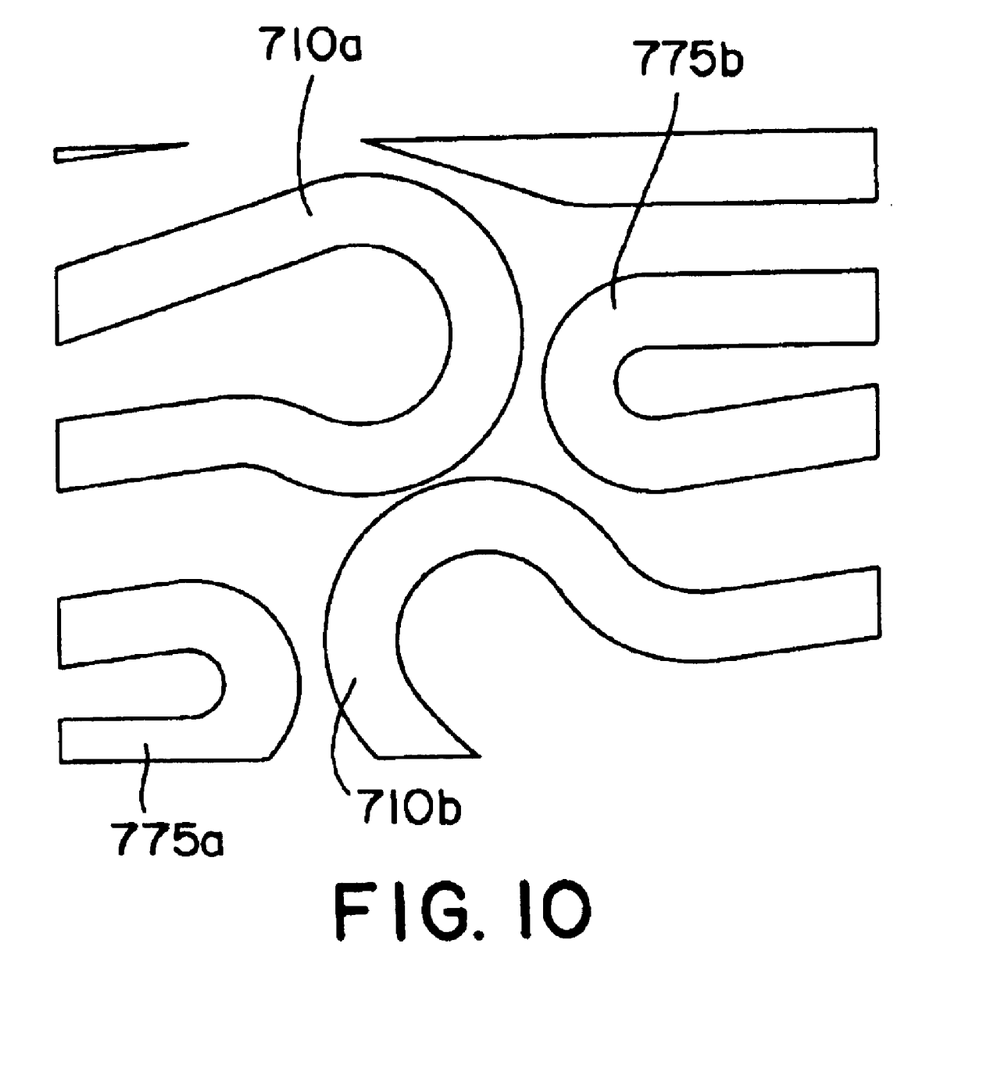
FIG. 10 illustrates how certain first elements and certain second elements nestle when the stent is crimped.

In some embodiments of the present invention, when the stent is crimped, a portion of a second expandable element 350 nests within a portion of the first expandable element 300. For example, as is shown in FIG. 7, a portion of second expandable element 350 nests within a portion of element 300. Specifically, in this embodiment, which is illustrative and not exhaustive of the present invention, a portion of filament 770b and 775b nest within the concave portions of filament 710a and 700a. This example illustrates some, but not necessarily all, of the nesting features of the present invention In some embodiments of the present invention, when the stent is crimped, portions from two separate first expandable elements 300 may nestle between the same portions of two separate second expandable segments 350. As is shown in FIG. 10, part of one first expandable element, namely filament 710a and part of a second first expandable element 710b, both of which comprise heads for R-shaped structures 730a and 730b (see also FIGS. 4a and 4b) nestle between filaments 775a and 775b, which are each part of a separate second expandable elements 350. FIG. 10 illustrates some, but not necessarily all, of the nestling features of the geometry of the present invention.

As is illustrated by FIGS. 2, 3, 4a, 4b and 5, in some embodiments, not only is the filament 775a part of one second expandable element 350 which is in turn part of a second helical segment 150a, but also filament 710a is part of one first expandable segment 300 which is in turn part of a first helical segment 120a. Likewise, filament 775b is part of different second expandable element 350, which is part of a second second helical segment 150b and filament 710b is part of a second first expandable element 300, which is in turn part of another helical segment 120b. Thus, in one embodiment of the present invention portions of one first helical segment and portions of another first helical segment nestle, when the stent is crimped, between portions of two separate second helical segments.

Figure 8A:
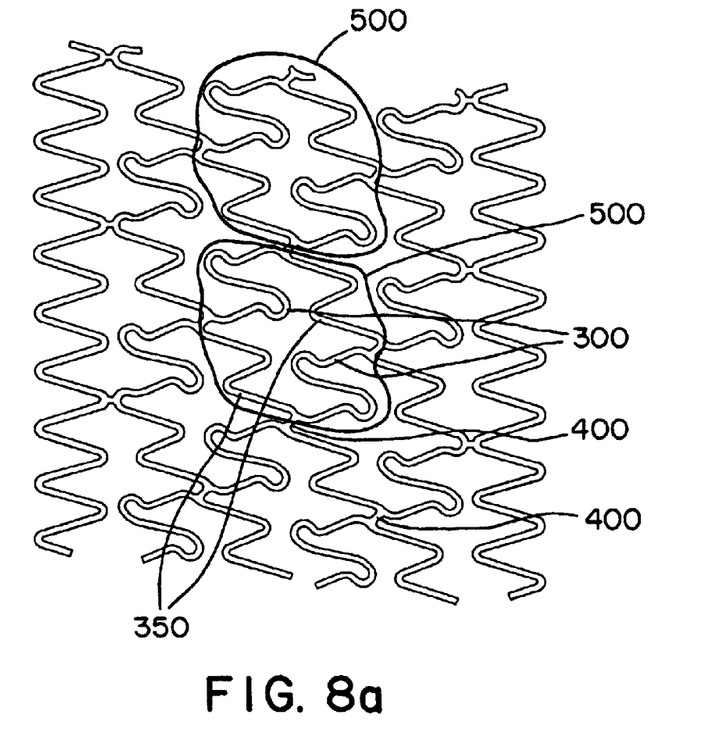
FIG. 8a is a planar view illustrating a plurality of cells that may be joined together to make one embodiment of the stent of the present invention.
Figure 8B:
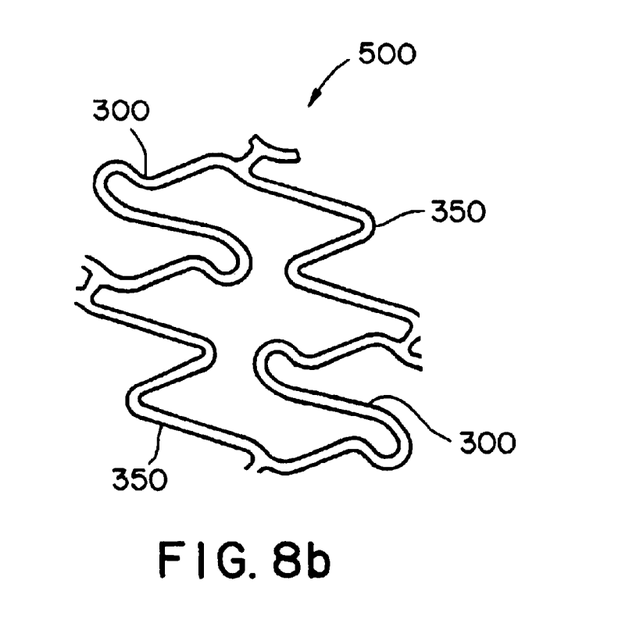

As is shown in FIG. 8a, the stent of the present invention, may in some embodiments, be comprised of a plurality of cells 500. In some embodiments, the cells 500 may be joined together by struts 400. Each cell 500 may be comprised of first elements 300 and second elements 350. In one embodiment, as is shown in FIG. 8b, each first element 300 is joined to two second elements 350, and each second element 350 is joined to two first elements 300. This results in a polygon, which may take many forms or may be amorphous. As is shown in FIGS. 2 and 8a, cells may be joined together so that the resulting stent has a plurality of helical segments, wherein at least one helical segment cross another. (See e.g. FIG. 2).

Cell geometry may be such that each cell expands at a relatively constant rate. For example, in the embodiment shown in FIG. 8a, each cell is comprised of a plurality of first expandable elements 300 and a plurality of second expandable elements 350. Each first element 300 is in turn comprised of a plurality of R-shaped elements 730a and 730b. The second expandable elements 350 in this illustrative embodiment are generally Z-shaped. During expansion, the R-shaped elements 730a and 730b expand at a slower initial rate than the Z-shaped elements. By staggering or alternating circumferentially first elements 300 and second elements 350, the stent expands circumferentially in a uniform manner because each cell circumferentially expands uniformly, notwithstanding that the elements 350 expand faster than the elements 300. The endzones may also expand at diffexent rates than the elements 300 and 350.

Figure 9:
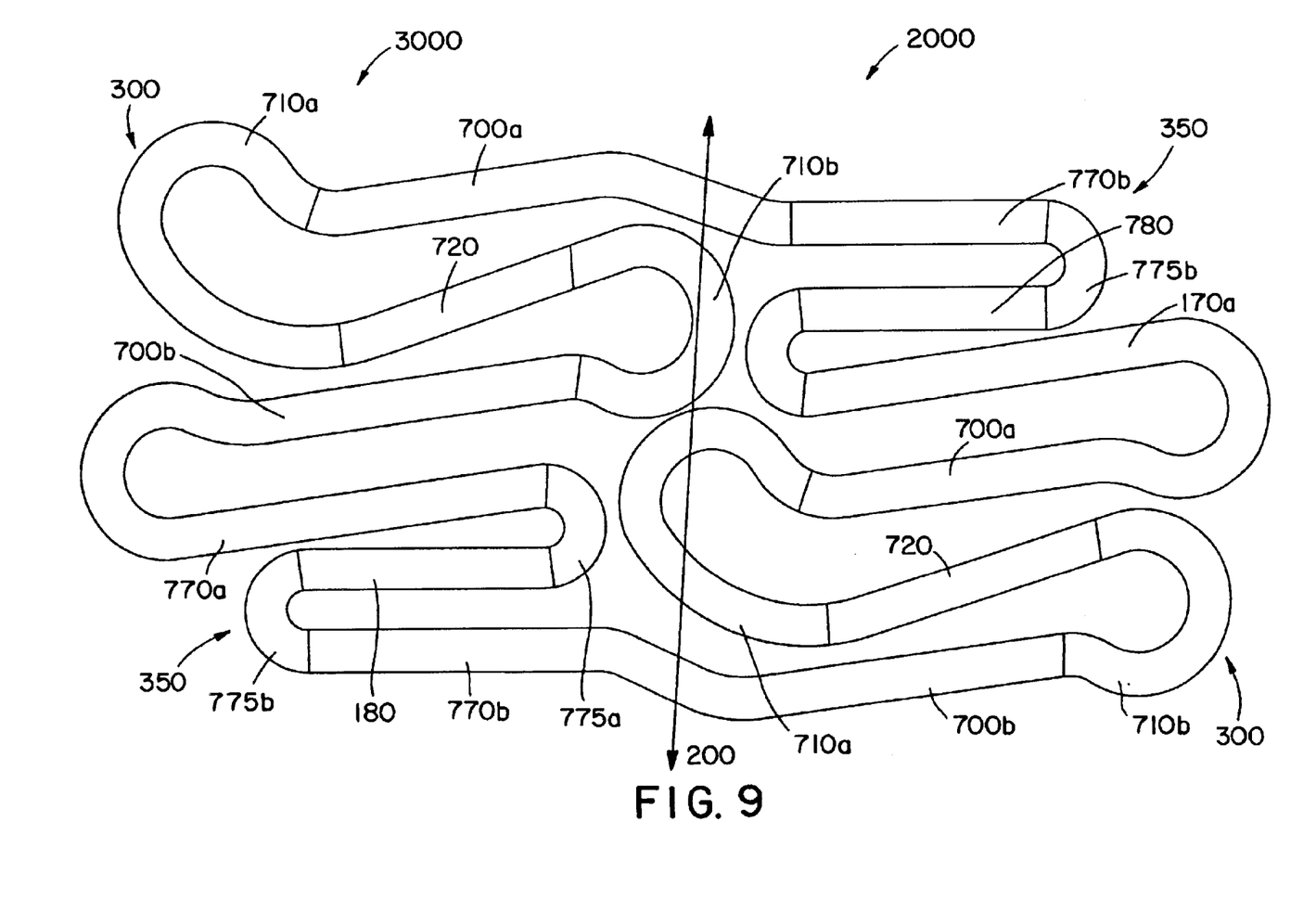
FIG. 9 is a planar view of the cell of FIG. 8a after the stent has been crimped.

As is shown in FIG. 9, when a stent according to the present invention is crimped, each cell circumferentially contracts. In this embodiment, which is included herein for illustrative purposes only and is not exhaustive of the present invention, when the stent is crimped, one portion of a first expandable element (e.g. at least portions of filaments 710a and 720) nests within another portion of the same first expandable element (e.g. at least portions of filament 700b) and portions of two separate first expandable elements 300 (e.g., filaments 710a and 710b) nestle between two separate second expandable elements 350. When the stent is expanded each cell expands uniformly along line 200, which is the circumferential dimension of the stent. (See FIG. 1). The second expandable elements 350 open at a faster rate than the first expandable elements 300, but since the first expandable elements are oriented diagonally, as are the second expandable elements, the right portion 2000 of the cell 500 expands at the same rate as the left portion 3000 of the cell 500. (See FIG. 9).

The foregoing embodiments and description is intended to illustrate the various and broad-ranging features of the present invention and is not intended to limit the scope or spirit of the present invention. The present invention may be embodied in numerous forms other than those specifically described above. For example, and without limitation, the first elements 300 and the second elements 350 may take numerous forms and shapes other than those shown. This may result in a first helical segment having a total filament length that is greater than or less than that of a second helical element. In addition, the stents of the present invention may be manufactured from materials with techniques that are readily known in the art, such as for example, by laser cutting tubes, which are manufactured from appropriate stent materials. Thus, although the embodiments described herein refer to different elements and segments within the same stent, those skilled in the art will recognize that the stent of the present invention may be comprised of a single continuous piece of material or it may be comprised of multiple disparate filaments or segment pieces joined together by well-known techniques.

We claim:

1. An expandable stent that is capable of being crimped onto a delivery device, the stent comprising a main body having a circumference, the main body comprising:
    a plurality of first helical segments having a circumferential dimension that expands when the stent is expanded and contracts when the stent is crimped; and
    a plurality of second helical segments having a circumferential dimension that expands when the stent is expanded and contracts when the stent is crimped;
    wherein, when the stent is crimped, a portion of one of the first helical segments and a portion of another of the first helical segments nestle between a portion of one second helical segment and a portion of another second helical segment; and
    wherein, when the stent is crimped, portions of a second helical segment nest within portions of a first helical segment.

2. The stent of claim 1, further comprising a first endzone and a second endzone, the endzones straddling the main body, and wherein the endzones and the first helical segments and the second helical segments expand at different rates when the stent is subjected to a radial expansion force.

3. The stent of claim 2, wherein the endzones comprise square outer edges.

4. The stent of claim 2, wherein the first helical segments form a first helical angle and the second helical segments form a second and different helical angle.

5. The stent of claim 4, wherein the first helical segments are comprised of a plurality of first expandable elements and wherein the second helical segments are comprised of a plurality of second expandable elements, and wherein the second expandable elements expand at a faster rate than the first expandable elements.

6. The stent of claim 5, wherein, when the stent is subject to a radial expansion force, the main body expands an a uniform rate.

7. The stent of claim 6, wherein the stent has a crimped diameter of less than 2.0 mm and an expanded diameter of greater than 12 mm.

8. The stent of claim 6, wherein the first expandable elements are comprised of a plurality of substantially R-shaped structures.

9. The stent of claim 8, wherein the R-shaped elements share a common filament element and are inversely oriented to one another.

10. The stent of claim 9, wherein the second expandable elements are comprised of a plurality of linear segments joined together by curved segments.

11. The stent of claim 10, wherein the second expandable elements are substantially Z-shaped.

12. A balloon expandable cylindrically shaped stent having a geometry that allows the stent to be crimped onto a delivery device, the stent comprising:

a plurality of first expandable elements, the first expandable elements being expandable in a circumferential direction, the circumferential direction being parallel to the circumference of the stent;

a plurality of second expandable elements, the second expandable elements also being expandable in the circumferential direction;

a plurality of first struts for joining the first expandable elements together to form a plurality of first helical segments and joining the second expandable elements together to form second opposing helical segments, each first strut joining two first expandable elements and joining two second expandable elements;

wherein, when the stent is crimped, a portion of one of the first expandable elements nests within a portion of another the same first expandable element.

13. The stent of claim 12, wherein, when the stent is crimped, portions of two first expandable elements nestle between a portion of one of the second expandable elements and a portion of another second expandable element.

14. The stent of claim 13, wherein the first helical segments are oriented at a first helical angle and the second helical segments are oriented at a second and different helical angle.

15. The stent of claim 13, wherein the first helical segment has a total filament length differs from that of the second helical segment.

16. The stent of claim 13, further comprising square outer ends.

17. A stent having a generally cylindrical main body, the main body comprising:

a plurality of helical segments, at least one helical segment crossing another helical segment, wherein the helical segments contract and expand in a direction parallel to the circumference of the main body when the stent is crimped and expanded, wherein at least one helical segment is comprised of a plurality of R-shaped filaments and wherein the stent has a crimped diameter and an expanded diameter that is 3–6 times the crimped diameter.

18. A stent having a generally cylindrical main body, the main body comprising:

a plurality of helical segments, at least one helical segment crossing another helical segment, wherein the helical segments contract and expand in a direction parallel to the circumference of the main body when the stent is crimped and expanded, wherein at least a portion of one helical segment nestles between two other helical segments when the stent is crimped and wherein the stent has a crimped diameter and an expanded diameter that is 3–6 times the crimped diameter.

19. A balloon expandable stent having a geometry for crimping it to a delivery device, the stent comprising:

a plurality of contiguous filaments forming a plurality of circumferentially expandable helical segments, at least one helical segment having a first portion that nests within another portion of the same helical segment and a second portion that nestles between two other helical segments.

20. The stent of claim 19, wherein the stent has a crimped diameter and an expanded diameter 3–6 times the crimped diameter.

21. The stent of claim 20, wherein the stent, in its expanded state, has a stent to vessel ratio greater than approximately 15%.

22. A stent comprising:

a plurality of cells, each cell comprised of:

a plurality of first elements;

a plurality of second elements, wherein each first element is connected to two second elements and each second element is connected to two first elements, thereby forming a polygon, wherein when the stent is crimped at least a portion of one of the first elements nestles between portions of two second elements; and a plurality of struts connecting one cell to another.

23. The stent of claim 22, wherein the second elements expand at a greater rate than the first elements, and wherein the cells uniformly circumferentially expand.

24. The stent of claim 23, wherein the first element has at least a portion that is generally R-shaped.

25. The stent of claim 24, wherein the cells are joined together by struts to form:

a plurality of first helical segments that are comprised of a plurality of first elements; and a plurality of second helical segments that are comprised of a plurality of second elements.

26. The stent of claim 25, wherein the struts are integral parts of the first and second elements.

27. The stent of claim 23, wherein the second elements are generally Z-shaped.

28. A stent comprising:

a plurality of first elements comprised of one or more generally R-shaped filament segments;

a plurality of second elements comprised of one or more generally Z-shaped filament segments;

a plurality of struts joining at least some the first elements together to form one or more generally first helical segments and joining at least some of the second elements to form one or more generally helical second segments, wherein the struts are integral parts of the first and second elements.

29. The stent of claim 28, wherein the first and second elements and the struts are portions of the same contiguous piece of material.

30. The stent of claim 29, further comprising endzones.

31. The stent of claim 30, wherein the endzones are part of the same contiguous piece of material.

32. The stent of claim 31, wherein the first and second elements expand in a circumferential direction at different rates when the stent is subject to a radially expansive force.

33. The stent of claim 32, wherein the stent uniformly expands circumferentially when subject to a radially expansive force.

* * * * *

UNITED STATES PATENT AND TRADEMARK OFFICE
CERTIFICATE OF CORRECTION

PATENT NO. : 6,821,292 B2  
APPLICATION NO. : 10/071071  
DATED : November 23, 2004  
INVENTOR(S) : Pazienza et al.

Page 1 of 1

It is certified that error appears in the above-identified patent and that said Letters Patent is hereby corrected as shown below:

On the title page item (56),
References Cited, INID
"2002/0116644" should read --2002/0116044--.

Col. 6:
Line 49: "expands an a" should read --expands at a--.

Col. 7:
Lines 14-15: "a portion of another" should read --another portion of--.
Line 25: "filament length differs" should read --length that differs--.
Line 28: "ends" should read --edges--.
Line 53: "crimping it to" should read --crimping onto--.

Col. 8:
Line 22: "the first element" should read --each first element--.
Line 25: Insert --the-- before "struts".
Line 28: Insert --the-- before "first".
Line 30: Insert --the-- before "second".
Line 41: "generally first helical" should read --generally helical first--.

Signed and Sealed this

Fifth Day of May, 2009

JOHN DOLL
*Acting Director of the United States Patent and Trademark Office*

(12) INTER PARTES REEXAMINATION CERTIFICATE (999th)
United States Patent
Pazienza et al.

(10) Number: US 6,821,292 C1
(45) Certificate Issued: Nov. 18, 2014

(54) CRIMPABLE INTRALUMINAL ENDOPROSTHESIS HAVING HELICAL ELEMENTS

(75) Inventors: John D. Pazienza, Pompano Beach, FL (US); Peter G. Piferi, Plantation, FL (US); Gary J. Becker, Miami, FL (US)

(73) Assignee: Orbusneich Medical, Inc., Fort Lauderdale, FL (US)

Reexamination Request:
No. 95/001,940, Mar. 22, 2012

Reexamination Certificate for:
Patent No.: 6,821,292
Issued: Nov. 23, 2004
Appl. No.: 10/071,071
Filed: Feb. 8, 2002

Certificate of Correction issued May 20, 2009

Related U.S. Application Data

(63) Continuation-in-part of application No. 09/511,481, filed on Feb. 23, 2000, now Pat. No. 7,108,714, which is a continuation of application No. 09/094,402, filed on Jun. 10, 1998, now Pat. No. 6,117,165.

(60) Provisional application No. 60/267,778, filed on Feb. 9, 2001.

(30) Foreign Application Priority Data

Jun. 13, 1997 (EP) ..................................... 97201799
May 6, 1998 (EP) ..................................... 98201446

(51) Int. Cl.
*A61F 2/06* (2013.01)
*A61F 2/91* (2013.01)
*A61F 2/88* (2006.01)

(52) U.S. Cl.
CPC ..... *A61F 2/91* (2013.01); *A61F 2/88* (2013.01)
USPC ........ 623/1.15; 623/1.17; 623/1.22; 623/1.16

(58) Field of Classification Search
None
See application file for complete search history.

(56) References Cited

To view the complete listing of prior art documents cited during the proceeding for Reexamination Control Number 95/001,940, please refer to the USPTO's public Patent Application Information Retrieval (PAIR) system under the Display References tab.

*Primary Examiner* — Cary Wehner (57) ABSTRACT

A stent having helical elements, a geometry for improved crimping, and a good stent-to-vessel ratio is disclosed. In one embodiment, the stent has a plurality of first helical segments and a plurality of second opposing helical segments. The first helical segments are comprised of a plurality of first expandable elements and the second helical segments are comprised of a plurality of second helical elements. The expandable elements are joined to each other by a plurality of struts. When the stent is crimped a portion of one of the first expandable elements nest within another portion of the same expandable element and a portion of two first expandable elements nestle between the same two portions of second expandable elements.

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-14, 16-20, 22 and 28-33 are cancelled.

Claims 15 and 23 are determined to be patentable as amended.

Claims 24-27, dependent on an amended claim, are determined to be patentable.

Claim 21 was not reexamined.

15. [The stent of claim 13,] *A balloon expandable cylindrically shaped stent having a geometry that allows the stent to be crimped onto a delivery device, the stent comprising:*

*a plurality of first expandable elements, the first expandable elements being expandable in a circumferential direction, the circumferential direction being parallel to the circumference of the stent;*

*a plurality of second expandable elements, the second expandable elements also being expandable in the circumferential direction; and*

*a plurality of first struts for joining the first expandable elements together to form a plurality of first helical segments and joining the second expandable elements together to form second opposing helical segments, each first strut joining two first expandable elements and joining two second expandable elements,* wherein the first helical segment has a total filament length that differs from that of the second helical segment;

*wherein, when the stent is crimped, a portion of one of the first expandable elements nests within a portion of the same first expandable element and portions of two first expandable elements nestled between a portion of one of the second expandable elements and a portion of another second expandable element.*

23. [The stent of claim 22,] *A stent comprising: a plurality of cells, each cell comprised of:*

*a plurality of first elements; a plurality of second elements,*
*wherein each first element is connected to two second elements and each second element is connected to two first elements, thereby forming a polygon,*
*wherein when the stent is crimped at least a portion of one of the first elements nestles between portions of two second elements; and a plurality of struts connecting one cell to another,* wherein the second elements expand at a greater rate than the first elements, and wherein the cells uniformly circumferentially expand.

* * * * *